United States Patent [19]

Colquhoun et al.

[11] Patent Number: 4,612,399
[45] Date of Patent: Sep. 16, 1986

[54] PURIFICATION OF 4-FLUORO-4'-HYDROXYBENZOPHENONE

[75] Inventors: Howard M. Colquhoun; David F. Lewis, both of Cheshire, England

[73] Assignee: Imperial Chemical Industries PLC, London, England

[21] Appl. No.: 733,362

[22] Filed: May 13, 1985

[30] Foreign Application Priority Data

May 24, 1984 [GB] United Kingdom ............... 8413314

[51] Int. Cl.[4] ............................................. C07C 45/81
[52] U.S. Cl. .................................................. 568/324
[58] Field of Search ......................................... 568/324

[56] References Cited

U.S. PATENT DOCUMENTS 3,403,183  9/1968  Dobraty et al. ............... 568/324
3,830,845  8/1974  Arimoto et al. .............. 568/324

FOREIGN PATENT DOCUMENTS 69598    3/1982  European Pat. Off. ............ 568/324
75390    5/1983  European Pat. Off. ............ 568/324
59-31729 2/1984  Japan ........................... 568/324
1574441  6/1968  United Kingdom ............... 568/324

OTHER PUBLICATIONS

Attwood et al., (Poly. Preprints, American Chemical Society, Div. Polym. Chem, vol. 20, (1979) pp. 191-194).

Primary Examiner—James H. Reamer
Attorney, Agent, or Firm—Cushman, Darby & Cushman

[57] ABSTRACT

A mixture of isomers of fluoro-4'-hydroxybenzophenone are dissolved in an aqueous solution of a base, for example sodium hydroxide, and sufficient acid is added to reduce the pH to not less than 9 and to precipitate 4-fluoro-4'-hydroxybenzophenone having a reduced proportion of other isomers.

10 Claims, No Drawings

PURIFICATION OF 4-FLUORO-4'-HYDROXYBENZOPHENONE

The present invention relates to a purification process and, in particular, to a process for purifying a mixture of isomers to obtain a desired isomer.

4-fluoro-4'-hydroxybenzophenone may be used as a precursor of poly (aryl ether ketone). Copending British Patent Application Nos. 8315610 and 8315612 (now European Patent Applications Publication Nos. 128693 and 128692 respectively and corresponding with U.S. applications Ser. No. 616,895 and Ser. No. 616,894, both filed June 4, 1984, respectively.), describe processes for the production of 4-fluoro-4'-hydroxybenzophenone. These processes produce a mixture of isomers of fluorohydroxybenzophenone the major proportion being the desired 4-fluoro-4'-hydroxybenzophenone with a minor proportion of 2-fluoro-4'-hydroxybenzophenone. However, the presence of such other isomers is undesired if the benzophenone compound is to be used for the preparation of poly (aryl ether ketone) since the presence of isomers such as 2-fluoro-4'-hydroxybenzophenone can have a deleterious effect on the properties of the poly (aryl ether ketone). Hence, it is desirable to obtain 4-fluoro-4'-hydroxybenzophenone of a high degree of purity, preferably, at least 99% by weight of the desired isomer.

British Patent Specification No. 1574441 describes a process for the production of hydroxybenzophenones, including halohydroxybenzophenones. In the working examples, the crude product is purified by dissolving in an aqueous alkaline solution, sodium dithionite and charcoal are added, the mixture is filtered, poured into an excess of acetic acid and cold water added. A crystalline product is obtained, this is dissolved in methylated spirit, treated again with charcoal and water added to cause crystallisation. Attwood et al (Poly. Preprints, American Chemical Society, Div Polym. Chem, Vol 20 (1979) pages 191-194) used 4-fluoro-4'-hydroxybenzophenone which had been purified by decolourising with charcoal and repeated recrystallisation from xylene. Similarly, in the processes of European Patent Applications Publication Nos. 69598 and 75390, substituted benzophenones are purified by recrystallisation. We have now found that the purity of 4-fluoro-4'-hydroxybenzophenone can be improved without effecting recrystallisation of the material.

According to the present invention there is provided a process for increasing the purity of 4-fluoro-4'-hydroxybenzophenone, which process comprises dissolving a mixture of isomers of fluoro-4'-hydroxybenzophenone, including 4-fluoro-4'-hydroxybenzophenone, in an aqueous solution of a base, then adding an acid to to the obtained solution to reduce the pH of the solution to not less than 9, and to give a precipitate which is separated from the solution.

Typically, the isomeric material used in the process of the present invention is 4-fluoro-4'-hydroxybenzophenone containing 1 to 10% by weight, relative to the total material, of 2-fluoro-4'-hydroxybenzophenone.

The base used can be any base which is capable of forming a water soluble salt from the mixture of hydroxybenzophenone isomers. Hence, the base is preferably a compound of an alkali metal since compounds of the alkali metals generally have satisfactory solubility. The base is conveniently a compound of potassium or sodium. Suitable bases include alkali metal hydroxides and carbonates but, since acidification of solutions obtained using carbonates can give foaming, the use of carbonates is not preferred.

Any medium to strong acid may be added to the aqueous solution. Suitable acids include inorganic acids such as hydrochloric acid, sulphuric acid, phosphoric acid and carbonic acid and organic acids such as carboxylic acids and sulphonic acids such as methanesulphonic acid and trifluoromethanesulphonic acid. The acid used may be a concentrated acid but we prefer to use dilute aqueous acids, for example from 0.1 to 5 Molar.

The acid is preferably added in an amount which corresponds to at least 80% and not more than 98% of that required to give essentially complete precipitation of the mixture of fluoro-4'-hydroxybenzophenone isomers. Hence, whilst the process of the present invention can be effected by monitoring the pH of the solution and adding the acid to reach a desired lower pH, it may be more convenient to determine, or calculate, the amount of acid required to precipitate essentially all of the mixture of hydroxybenzophenone isomers and then add from 80 up to 98% of this amount.

The process of the present invention may be effected in a single step or may be repeated a further one or more times. Satisfactory purity can be achieved in a single step with recovery of 90% by weight of the starting mixture of hydroxybenzophenone isomers. However, improved purity can be achieved, also with recovery of about 90% by weight of the starting mixture, by effecting two purification steps in accordance with the present invention.

It has been found that, as the acid is added to the solution of the hydroxybenzophenone isomers in the base, the product initially precipitated is 4-fluoro-4'-hydroxybenzophenone having a low proportion, typically less than 0.5% by weight of 2-fluoro-4'-hydroxybenzophenone. As the addition of acid is continued, the material precipitated contains an increasing proportion of 2-fluoro-4'-hydroxybenzophenone. The addition of the final 10% of acid, to give complete precipitation, typically results in the precipitation of a material containing at least 50% of the 2-fluoro-4'-hydroxybenzophenone present in the original mixture.

It will be appreciated that the purity of the recovered 4-fluoro-4'-hydroxybenzophenone is dependent not only on the proportion of material recovered but also on the impurity level of the initial isomer mixture and the concentration of the reagents used.

Certain concentrated acids may react adversely with the hydroxybenzophenone compound, for example by sulphonation or oxidation. Accordingly, we prefer to avoid the use of such concentrated acids, although other concentrated acids, such as concentrated hydrochloric acid, have been used successfully in the process of the present invention. However, the results achieved with dilute acids are generally more satisfactory. It is generally preferred to use both the base and the acid in concentrations of from 0.1 up to 20 molar in water, particularly from 0.5 up to 5 molar, for example with molar solutions of both base and acid.

The process of the present invention may be effected at low or elevated temperature, for example from 0° C. up to 100° C., and is conveniently effected at ambient temperature.

The process of the present invention may be effected in a single step by adding the acid in an amount to achieve 90% recovery of the hydroxybenzophenone mixture. However, by effecting two steps, in each of which 95% of the hydroxybenzophenone mixture is recovered, essentially the same proportion of the initial hydroxybenzophenone is recovered which contains a lower proportion of the undesired 2-fluoro-4'-hydroxybenzophenone isomer.

Using a molar solution of sodium hydroxide to dissolve a hydroxybenzophenone compound containing between 1 and 4% of 2-fluoro-4'-hydroxybenzophenone, and adding molar hydrochloric acid, it has been found that about 95% recovery of the hydroxybenzophenone compound, having an impurity level of not more than about 0.6%, can be achieved when sufficient acid has been added to lower the pH to 9.5. It will be appreciated that the proportion of material recovered, and the purity thereof, will vary in dependence on the base and acid used and the concentrations thereof. We have found that a precipitate is not formed until the pH has been reduced and, in general, precipitation does not occur until the pH is about 11.5 or below. Hence, we prefer that sufficient acid is added to reduce the pH to below 11.5.

The precipitate formed on adding the acid may be isolated by any known technique for separating a solid from a liquid medium. Conveniently the precipitate is isolated by filtration. The isolated precipitate may be washed with water and dried.

If desired, the purified product may be recrystallised from a suitable solvent such as toluene.

The present invention is further illustrated by the following, non-limiting, examples.

EXAMPLE 1

A. Preparation of 4-fluoro-4'-hydroxybenzophenone

This preparation was carried out in accordance with the procedure of our co-pending British Patent Application No. 8315610 (now European Patent Application Publication No. 128693).

A suspension of 4-hydroxybenzoic acid (69 g, 0.5 mol) in fluorobenzene (400 cm$^3$) was heated, in a nitrogen atmosphere, to 60° C. with stirring. Dimethylformamide (1 cm$^3$) and thionyl chloride (65 g, 0.55 mole) were added over a period of 30 minutes and the mixture was heated to 85° C. The suspension was stirred for two hours at 85° C. and then cooled to room temperature. The cold suspension was added, over a period of 30 minutes, to a stirred suspension of aluminum chloride (166 g, 1.25 mol) in fluorobenzene (100 cm$^3$) under nitrogen at 65° C. The temperature was raised to 85° C., during which time hydrogen chloride was evolved and the mixture became thicker. The mixture was stirred at 85° C. for 18 hours, at which time a solution had been formed. The solution was poured into one dm$^3$ of water at ambient temperature and the mixture was stirred. A solid separated. Unreacted fluorobenzene was recovered by distillation.

The solid product was filtered off, washed with water until acid free and dried to give a free flowing solid by passing a stream of air through the solid. The solid was dissolved in 50 cm$^3$ of 4% w/v aqueous sodium hydroxide solution and the solution was washed twice with 200 cm$^3$ of dichloromethane. The solution was acidified to a pH of about one by the addition of one molar hydrochloric acid. A precipitate was formed which was filtered off then washed repeatedly with water until the washings were acid free. The solid was then dried under vacuum at ambient temperature for 16 hours.

B. Purification of 4-fluoro-4'-hydroxybenzophenone

A sample of 4-fluoro-4'-hydroxybenzophenone (67.8 g), containing 1.2% of the 2-fluoro-4'-hydroxy isomer, was dissolved in 324 cm$^3$ of molar aqueous sodium hydroxide solution. Aqueous molar hydrochloric acid was added dropwise with stirring until the pH had fallen to 9.5. The precipitate was filtered off, washed with water (300 cm$^3$) and dried at 100° C. under vacuum. The yield was 63.1 g (93% recovery) and the level of the 2-fluoro-4'-hydroxy isomer had fallen to 0.5%. The procedure was repeated on the recovered material, giving 59.9 g of product containing 0.2% of the 2-fluoro-4'-hydroxy isomer.

This material was finally recrystallized from toluene (30 cm$^3$ for each gramme of solid) to give 53.9 g of product containing 0.1% of the 2-fluoro-4'-hydroxy isomer. It was subsequently discovered that the toluene was contaminated and contained a proportion of sodium hydroxide and it is the presence of this sodium hydroxide which caused the further reduction in the level of the 2-fluoro-4'-hydroxy isomer.

EXAMPLE 2

The procedure of stage B of Example 1 was repeated on a larger scale using a different sample of 4-fluoro-4'-hydroxybenzophenone.

A sample of 4-fluoro-4'-hydroxybenzophenone (147.8 g), containing 0.69% of the 2-fluoro-4'-hydroxy isomer, was dissolved in 703.6 cm$^3$ of molar aqueous sodium hydroxide solution. Aqueous molar hydrochloric acid was added dropwise, with stirring, until the pH had fallen to 9.5. A precipitate was formed and this was filtered off, washed with one dm$^3$ of water and dried at 100° C. under vacuum. The yield was 140.6 g (95% recovery) and the level of the 2-fluoro-4'-hydroxy isomer had fallen to 0.45%.

The recovered material was dissolved in 670.1 cm$^3$ of molar aqueous sodium hydroxide solution and aqueous molar hydrochloric acid was added until the pH had fallen to 9.6. The product was isolated as previously to give 131.1 g of material containing 0.19% of the 2-fluoro-4'-hydroxy isomer.

The material was recrystallised from 3 dm$^3$ of pure toluene to give 116.8 g of material with the same proportion of the 2-fluoro-4'-hydroxy isomer.

EXAMPLE 3

The procedure of stage B of Example 1 as repeated using only a single acidification step.

9.85 g of 4-fluoro-4'-hydroxybenzophenone containing 0.77% of the 2-fluoro-4'-hydroxy isomer was dissolved in 46 cm$^3$ of molar aqueous sodium hydroxide solution. Aqueous molar hydrochloric acid was added dropwise, with stirring, until the pH had fallen to 9.8. The precipitate was filtered off, washed and dried as in Example 1. The yield was 9.17 g and the level of the 2-fluoro-4'-hydroxy isomer was 0.36%.

The filtered solution was acidified further to pH 2. A yield of 0.34 g of a product containing 4.56% of the 2-fluoro-4'-hydroxy isomer was obtained.

EXAMPLE 4

A procedure similar to that of Example 3 was carried out using concentrated hydrochloric acid.

20 g of 4-fluoro-4'-hydroxybenzophenone containg 1.64% of the 2-fluoro-4'-hydroxy isomer was dissolved in 92.5 cm$^3$ of molar aqueous sodium hydroxide solution. Concentrated (9.6M) hydrochloric acid was added dropwise, with stirring, until the pH had fallen to 10.3. The precipitate was filtered off, washed with water and dried as in Example 1.

The yield was 18.46 g of a product containing 1.13% of the 2-fluoro-4'-hydroxy isomer.

EXAMPLE 5

A procedure similar to that of Example 3 was carried out using dilute aqueous acetic acid.

10.81 g of 4-fluoro-4'-hydroxybenzophenone containing 1.95% of the 2-fluoro-4'-hydroxy isomer was dissolved in 55 cm$^3$ of molar aqueous sodium hydroxide solution. Aqueous molar acetic acid was added dropwise, with stirring, until the pH had fallen to 9.75. The precipitate was filtered off, washed with water and dried as in Example 1. The yield was 9.93 g and the level of the 2-fluoro-4'-hydroxy isomer was 0.71%.

The filtered solution was acidified further to pH 1 to give 0.42 g of a product containing 15.17% of the 2-fluoro-4'-hydroxy isomer.

EXAMPLE 6

A procedure similar to that of Example 3 as carried out using aqueous potassium hydroxide solution.

10 g of 4-fluoro-4'-hydroxybenzophenone containing 1.96% of the 2-fluoro-4'-hydroxy isomer was dissolved in 50 cm$^3$ of molar aqueous potassium hydroxide solution. Aqueous molar hydrochloric acid was added dropwise with stirring, until the pH had fallen to 9.6. The precipitate was filtered off, washed and dried as in Example 1. The yield was 9.35 g of a product containing 0.475 of the 2-fluoro-4'-hydroxy isomer.

The filtered solution was acidified further to pH 1 to give 0.47 g of a product containing 15% of the 2-fluoro-4'-hydroxy isomer.

EXAMPLE 7

This example illustrates the effect of decreasing pH on the amount of product recovered and the purity of that product.

10.81 g of 4-fluoro-4'-hydroxybenzophenone containg 1.88% of the 2-fluoro-4'-hydroxy isomer was dissolved in 154 cm$^3$ of a 0.33M aqueous sodium hydroxide solution. Aqueous molar hydrochloric acid was added dropwise with stirring. The addition of acid was interrupted from time to time to measure the pH of the solution using a calibrated pH meter and to separate off any precipitate which had been formed. The precipitate was washed and dried and the isomeric composition was determined. The results are given in the following Table.

TABLE

| Sample (a) | Acid Added (cm$^3$) | pH | Wt of ppt (b) | % Composition (c) 4,4' | 2,4' |
|---|---|---|---|---|---|
| 0 | 0 | 12.7 | 0 | — | — |
| 1 | 4 | 11.6 | 0 | — | — |
| 2 | 6 | 10.7 | 1.0 | 99.79 | 0.21 |
| 3 | 10 | 10.7 | 1.0 | 99.81 | 0.19 |
| 4 | 15 | 10.7 | 1.0 | 99.74 | 0.26 |
| 5 | 20 | 10.6 | 1.0 | 99.65 | 0.35 |
| 6 | 25 | 10.4 | 1.0 | 99.60 | 0.40 |
| 7 | 30 | 10.2 | 1.0 | 99.51 | 0.49 |
| 8 | 35 | 9.8 | 0.90 | 99.36 | 0.64 |
| 9 | 40 | 9.7 | 0.93 | 99.04 | 0.91 |
| 10 | 45 | 9.1 | 0.93 | 98.39 | 1.61 |
| 11 | 50 | 3.7 | 0.51 | 94.18 | 5.82 |

(a) Sample 0 is the initial solution of fluorohydroxybenzophenone in the sodium hydroxide solution.
(b) Weight of precipitate (in grammes) as determined by filtration of the solution after each further addition of acid.
(c) 4,4' means 4-fluoro-4'-hydroxybenzophenone.
2,4' means 2-fluoro-4'-hydroxybenzophenone.

The composition is of the sample precipitated and separated after each addition of acid.

It should be appreciated that although successive samples contain progressively larger proportions of the 2-fluoro-4'-hydroxy isomer, the composition of the total product separated does not show such a rapid change. Hence, although sample 10 contains 1.61% of the 2-fluoro-4'-hydroxy isomer, the total product of aggregating samples 1 to 10 contains 0.56% of the 2-fluoro-4'-hydroxy isomer.

We claim:

1. A process for increasing the purity of 4-fluoro-4'-hydroxybenzophenone which comprises dissolving a mixture of isomers of fluoro-4'-hydroxybenzophenone, including 4-fluoro-4'-hydroxybenzophenone, in an aqueous solution of a base to obtain a solution of the isomers, adding an acid to the obtained solution to reduce the pH of the solution and to give a precipitate, adding sufficient of the acid to reduce the pH of the solution to not less than 9, and separating the precipitate formed from the solution.

2. The process of in claim 1 wherein the base is an alkali metal hydroxide or carbonate.

3. The process of claim 1 wherein the acid is hydrochloric acid, sulphuric acid, phosphoric acid, carbonic acid, a carboxylic acid, methanesulphonic acid or trifluoromethanesulphonic acid.

4. The process of claim 1 wherein the acid is added in an amount which corresponds to at least 80%, and not more than 98%, of that required to give essentially complete precipitation of the mixture of fluoro-4'-hydroxybenzophenone isomers.

5. The process of claim 4 which is effected in a single step by the addition of sufficient acid to recover not more than 90% by weight of the mixture of fluoro-4'-hydroxybenzophenone isomers.

6. The process as claim 4 which is effected by adding sufficient acid to recover not more than 95% by weight of the mixture of fluoro-4'-hydroxybenzophenone isomers and repeating the process using the material recovered.

7. The process of claim 1 wherein the base and acid are used in concentrations of from 0.1 up to 5 molar in water.

8. The process of claim 1 wherein sufficient acid is added to reduce the pH to below 11.5.

9. The process of claim 1 wherein the acid is added to reduce the pH to not less than 9.5.

10. The process of claim 1 which is carried out at a temperature in the range from 0° C. up to 100° C.

* * * * *